US005785950A

United States Patent [19]

Kaufman et al.

[11] Patent Number: 5,785,950
[45] Date of Patent: *Jul. 28, 1998

[54] HIGHLY FLUORINATED, CHLORO-SUBSTITUTED ORGANIC COMPOUND-CONTAINING EMULSIONS AND METHODS OF MAKING AND USING THEM

[75] Inventors: Robert J. Kaufman; Thomas J. Richard, both of University City, Mo.; George G. I. Moore, Afton; Richard M. Flynn, Mahtomedi, both of Minn.

[73] Assignees: HemaGen/PFC, St. Louis, Mo.; Minnesota Mining & Manufacturing Co., St. Paul, Minn.

[*] Notice: The term of this patent shall not extend beyond the expiration date of Pat. No. 5,420,359.

[21] Appl. No.: 244,804

[22] PCT Filed: Dec. 11, 1992

[86] PCT No.: PCT/US92/10736

§ 371 Date: Oct. 12, 1994

§ 102(e) Date: Oct. 12, 1994

[87] PCT Pub. No.: WO93/11868

PCT Pub. Date: Jun. 24, 1993

Related U.S. Application Data

[63] Continuation-in-part of Ser. No. 806,692, Dec. 12, 1991, Pat. No. 5,403,575.
[51] Int. Cl.$^6$ .................. A61K 31/02; A61K 43/00; A61K 49/04; B01J 13/00
[52] U.S. Cl. .................. 424/1.89; 252/312; 252/314; 424/9.37; 514/757; 514/832; 514/833; 514/942; 514/943
[58] Field of Search .................. 252/311, 312; 514/832, 833, 942, 943, 757; 424/1.89, 9.37

[56] References Cited

U.S. PATENT DOCUMENTS

| | | |
|---|---|---|
| 2,055,083 | 9/1936 | Klein et al. . |
| 2,490,764 | 12/1949 | Benning et al. . |
| 3,435,078 | 3/1969 | Nychka et al. . |
| 3,456,024 | 7/1969 | Loree et al. . |
| 3,739,033 | 6/1973 | Anello et al. . |
| 3,778,381 | 12/1973 | Rosano et al. .................. 252/311 |
| 3,793,450 | 2/1974 | Schnell .................. 424/195.1 X |
| 3,823,091 | 7/1974 | Samejima et al. .................. 252/312 |
| 3,911,138 | 10/1975 | Clark, Jr. .................. 514/746 |
| 3,914,294 | 10/1975 | Bernstein et al. . |
| 3,942,527 | 3/1976 | Li .................. 604/4 |
| 3,958,014 | 5/1976 | Watanabe et al. .................. 424/366 |
| 3,962,439 | 6/1976 | Yokoyama et al. .................. 424/248 |
| 3,975,512 | 8/1976 | Long, Jr. .................. 424/9.4 |
| 3,989,843 | 11/1976 | Chabert et al. .................. 424/325 |
| 3,993,581 | 11/1976 | Yokoyama et al. .................. 252/312 |
| 4,073,879 | 2/1978 | Long, Jr. .................. 424/9.4 |
| 4,073,943 | 2/1978 | Wretlind et al. .................. 424/358 |
| 4,104,314 | 8/1978 | Terrell . |
| 4,105,798 | 8/1978 | Moore et al. .................. 424/352 |
| 4,110,474 | 8/1978 | Lagow et al. .................. 424/350 |
| 4,186,253 | 1/1980 | Yokoyama et al. .................. 435/240 |
| 4,252,827 | 2/1981 | Yokoyama et al. .................. 514/943 X |
| 4,285,928 | 8/1981 | Wada et al. .................. 424/9.4 |
| 4,289,499 | 9/1981 | Clark, Jr. et al. . |
| 4,325,972 | 4/1982 | Geyer et al. .................. 424/325 |
| 4,337,211 | 6/1982 | Ezzell et al. . |
| 4,366,169 | 12/1982 | White .................. 424/285 |
| 4,395,393 | 7/1983 | Schmolka .................. 424/78 |
| 4,397,870 | 8/1983 | Sloviter .................. 424/325 |
| 4,423,061 | 12/1983 | Yokoyama et al. .................. 424/274 |
| 4,423,077 | 12/1983 | Sloviter .................. 425/325 |
| 4,425,347 | 1/1984 | Yokoyama et al. .................. 424/256 |

(List continued on next page.)

FOREIGN PATENT DOCUMENTS

| | | |
|---|---|---|
| 0051526 | 5/1982 | European Pat. Off. . |
| 0080716 | 6/1983 | European Pat. Off. . |
| 0089232 | 9/1983 | European Pat. Off. . |
| 0144434 | 6/1985 | European Pat. Off. . |
| 0158996 | 10/1985 | European Pat. Off. . |
| 190393 | 8/1986 | European Pat. Off. . |
| 0220152 | 4/1987 | European Pat. Off. . |
| 0220153 | 4/1987 | European Pat. Off. . |
| 0231070 | 8/1987 | European Pat. Off. . |
| 295582 | 12/1988 | European Pat. Off. . |
| 440925 | 8/1991 | European Pat. Off. . |

(List continued on next page.)

OTHER PUBLICATIONS

U.S. application No. 08/132,787, Moore et al., filed Oct. 1993.

Journal of Organic Chemistry, vol. 56, No. 22, 25 Oct. 1991, Easton US, pp. 6348–6351, Chang–Ming Hu et al., "Redox–Initiated Per(poly) fluoroalkylation of Olefins by Per(poly) Fluoroalkyl Chlorides", see p. 6350, col. 1, penultimate paragraoh.

Journal of Organic Chemistry, vol. 35, No. 11, Nov. 1970, Easton US, pp. 3730–3733, L.R. Anderson et al. "Perhaloakyl Hypochlorites and Pentafluorosulfur Hypochlorite.

(List continued on next page.)

*Primary Examiner*—Richard D. Lovering
*Attorney, Agent, or Firm*—Fish & Neave

[57] ABSTRACT

This invention relates to compositions comprising highly fluorinated, chloro-substituted, non-cyclic organic compounds having 7 to 9 carbon atoms and to processes of making and using them. More particularly, this invention relates to emulsions comprising those highly fluorinated, chloro-substituted organic compounds. This invention also related to emulsion comprising noncyclic perfluorochlorethers having 7 to 10 carbon atoms, preferably 7 to 9 carbon atoms. These novel emulsions have various medical and oxygen transport applications. They are especially useful medically as contrast media, for various biological imaging modalities such as nuclear magnetic resonance, ultrasound, x-ray, computed tomography, $^{19}$F-magnetic resonance imaging, and position emission tomography, as oxygen transport agents or "artificial bloods," in the treatment of heart attack, stroke, and other vascular obstructions, as adjuvants to coronary angioplasty and in cancer radiation treatment and chemotherapy.

23 Claims, 1 Drawing Sheet

U.S. PATENT DOCUMENTS

| | | | |
|---|---|---|---|
| 4,443,480 | 4/1984 | Clark, Jr. | 424/352 |
| 4,446,154 | 5/1984 | Osterholm | 424/350 |
| 4,452,818 | 6/1984 | Haidt | 424/352 |
| 4,461,717 | 7/1984 | Moore | 252/312 |
| 4,486,417 | 12/1984 | Sugimoto et al. | 424/180 |
| 4,497,829 | 2/1985 | Sloviter | 514/672 |
| 4,510,335 | 4/1985 | Lagow et al. | 252/312 X |
| 4,526,969 | 7/1985 | Yokoyama et al. | 546/164 |
| 4,534,978 | 8/1985 | Yokoyama et al. | 514/429 |
| 4,542,147 | 9/1985 | Yokoyama et al. | 514/411 |
| 4,562,183 | 12/1985 | Tatlow et al. | 514/214 |
| 4,569,784 | 2/1986 | Moore | 252/315.1 |
| 4,591,599 | 5/1986 | Yokoyama et al. | 514/413 |
| 4,599,343 | 7/1986 | Yokoyama et al. | 514/299 |
| 4,657,532 | 4/1987 | Osterholm | 604/24 |
| 4,686,024 | 8/1987 | Scherer, Jr. et al. | 204/157.95 |
| 4,755,567 | 7/1988 | Bierschenk et al. | |
| 4,808,651 | 2/1989 | Blickle et al. | 524/366 |
| 4,815,466 | 3/1989 | Perlin | |
| 4,833,274 | 5/1989 | Caporiccio et al. | 570/137 |
| 4,859,747 | 8/1989 | Bierschenk et al. | |
| 4,865,836 | 9/1989 | Long, Jr. | 424/5 |
| 4,866,096 | 9/1989 | Schweighardt | 514/756 |
| 4,868,318 | 9/1989 | Scherer, Jr. et al. | 549/362 |
| 4,895,876 | 1/1990 | Schweighardt et al. | 514/747 |
| 5,053,536 | 10/1991 | Bierschenk et al. | 562/582 |
| 5,077,036 | 12/1991 | Long, Jr. | 514/832 X |
| 5,093,432 | 3/1992 | Bierschenk et al. | 525/331.6 |
| 5,114,703 | 5/1992 | Wolf et al. | 514/832 X |
| 5,116,599 | 5/1992 | Rogers, Jr. et al. | |
| 5,171,755 | 12/1992 | Kaufman et al. | 514/832 X |
| 5,393,513 | 2/1995 | Long, Jr. | 514/832 X |
| 5,403,575 | 4/1995 | Kaufman et al. | 424/1.89 |
| 5,420,359 | 5/1995 | Moore et al. | 568/684 |

FOREIGN PATENT DOCUMENTS

| | | |
|---|---|---|
| 2246262 | 5/1975 | France |
| 2494992 | 6/1982 | France |
| 2319971 | 11/1973 | Germany |
| 2315928 | 8/1974 | Germany |
| 51-26213 | 3/1976 | Japan |
| 58-32829 | 2/1983 | Japan |
| 84/03624 | 9/1984 | WIPO |
| 86/00810 | 2/1986 | WIPO |
| 89/10118 | 11/1989 | WIPO |
| 90/03357 | 4/1990 | WIPO |
| 90/03409 | 4/1990 | WIPO |
| 90/06296 | 6/1990 | WIPO |
| 93/11868 | 6/1993 | WIPO |

OTHER PUBLICATIONS

"Chemical Abstracts Eleventh Collective Index, Chemical Substances", American Chemical Society, see p. 32172CS, col., 1; Hexane, 1–chloro–1,1,2,2,3,3,4,4,5,5,6,6. (1987).

Adock, J.L. and W.D. Evans, J. Org. Chem. 1984, 49, 2719–23.

Banks, R.E., *Preparation, Properties, and Industrial Applications of Organofluoride Compounds*, pp. 93–95, John Wiley & Sons, New York (1982).

Hudlicky, M., *Chemistry of Organic Fluorine Compounds*, Second Edition, pp. 225–226, Ellis Horwood, New York (1992).

Lowe, K.C., "Perfluorochemicals in Medicine", *Chem, Ind.*, Feb. 4, 1991, pp. 83–88.

K. Yamanouchi and C. Heldebrant, "Perflurochemicals as a blood substitute, " CHEMTECH, Jun. 1992, pp. 354–359.

L. S. Chen and G. J. Chen, "Reaction of Phosphorus Pentachloride With Perhalo Carbonyl–Containing Compounds", *J. Fluor. Chem.*, 42, pp. 371–387 (1989) [Chen and Chen].

Q.-Y. Chen and Z.-M. Qiu, "Fluoroalkylation and Fluoroalkoxylation. Magnesium Single–Electron–Transfer Induced Synthesis of 2–Fluoroalkylpyrroles", *J. Fluor. Chem.*, 39, pp. 288–292 (1988) [Chen].

L. C. Clark et al., "Emulsions of Perfluorinated Solvents for Intravascular Gas Transport", *Fed. Proc.*, pp. 1468–1477 (1975) [Clark et al.].

D. E. Hammerschmidt and G. M. Vercelloti, "Limitation of Complement Activation by Perfluorocarbon Emulsions: Superiority of Lecithin Emulsified Preparations", *Chemical Abstracts*, vol. 109, Abstract 197120n (1988) [Hammerschmidt and Vercelloti].

R. N. Haszeldine, "The Synthesis of Flurorcarbons and of Fully Fluorinated Iodo–, Bromo–, and Chloro–alkanes", in *Reactions of Fluorocarbon Radicals*, Part XII, pp. 3761–3768 (1953) (Abstract No. 769) [Haszeldine].

R. Jeppsson, "Comparison of Pharmacological Effects of Some Local Anaesthetic Agents when using Water and Lipid Emulsion as Injection Vehicles", *Acta Pharmacol. et Toxicol.*, 36, pp. 299–311 (1975) [Jeppsson I].

R. Jeppsson, "Parabolic Relationship between Lipophilicity and Biological Activity of Aliphatic Hydrocarbons, Ethers and Ketones after Intravenous Injections of Emulsion Formulations into Mice", *Acta Pharmacol. et Toxicol.*, 37, pp. 56–64 (1975) [Jeppsson II].

R. Jeppsson and S. Ljungberg, "Anticonvulsant Activity in Mice of Diazepam in an Emulsion Formulation for Intravenous Administration", *Acta Pharmacol. et Toxicol.*, 36, pp. 312–320 (1975) [Jeppsson and Ljungberg].

R. Jeppsson and S. R össner, "The Influence of Emulsifying Agents and of Lipid Soluble Drugs on the Fractional Removal Rate of Lipid Emulsions from the Blood Stream of the Rabbit", *Acta Pharmacol. et Toxicol.*, 37, pp. 134–44 (1975) [Jeppsson and Rössner].

R. Jeppsson and G. I. Schoefl, "The Ultrastructure of Lipid Particles in Emulsions Prepared with Various Emulsifiers", *Aust. J. Exp. Biol. Med. Sci.*, 52, pp. 697–702 (1974). [Jeppsson and Schoefl].

R. Jeppsson and B. Sj öberg, "Compatibility of Parenteral Nutrition Solutions when mixed in a Plastic Bag", *Clin. Nutr.*, 2, pp. 149–158 (1984) [Jeppsson and Sj öberg].

R. Jeppsson et al., "Particle Size Distribution of a Fluorochemical Emulsion", in *Proceedings of the HS Symposium on Perfluorochemicals Medicine and Biology*, Huddings, Sweden, Apr. 28–29, 1977, V. Nováková et al., eds., pp. 108–113 (1977) [Jeppsson et al.].

S. Ljungberg and R. Jeppsson, "Intravenous Injection of Lipid Soluble Drugs", *Acta Pharm, Suecica*, 7, pp. 435–440 (1970) [Ljungberg and Jeppsson].

H. Ohyanagi and Y. Saitoh, "Development and Clinical Application of Perfluorochemical Artificial Blood", *Int. J. Artificial Organs*, 9, pp. 363–368 (1986) [Ohyanagi and Saitoh].

A. Wretlind, "Development of Fat Emulsions", *J. Parenter, Enteral Nutr.*, 5, pp. 230–235 (1981) [Wretlind II].

K. Yokoyama et al., "A. Perfluorochemical Emulsion as an Oxygen Carrier", *Artificial Organs*, 8, pp. 34–40 (1984) [Yokoyama et al.].

E. P. Wesseler et al., "The Solubility of Oxygen In Highly Fluorinated Liquids", *J. Fluor. Chem.*, 9, pp. 137–146 (1977) [Wesseler].

A. Wretlind, "Current Status of Intralipid and Other Fat Emulsions", in *Fat Emulsions Parenter, Nutr.*, H.–C. Meng et al., eds., American Medical Association, Chicago, IL, pp. 109–122 (1976) [Wretlind I].

A.Y. Zapevalov et al., "Synthesis And Reactions of Oxygen–Containing Organofluorine Compounds", *J. Org. Chem.*(trans.), 14(2), pp. 259–262 (1978) (CA 88: 190026a) [Zapevalov].

Q. Chen and Z. Qui, "Studies on Fluoroaklylation and Fluoroalkoxylation. 23. Single Electron Transfer–Induced Reaction of Perfluoroalkyl Iodides with Pyrrole by Zinc", (*Chemical Abstracts*, vol. 110; Abstract 75218a) (1989).

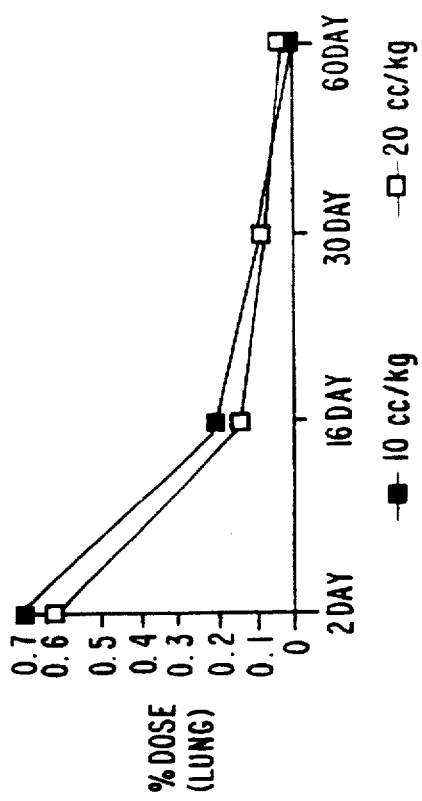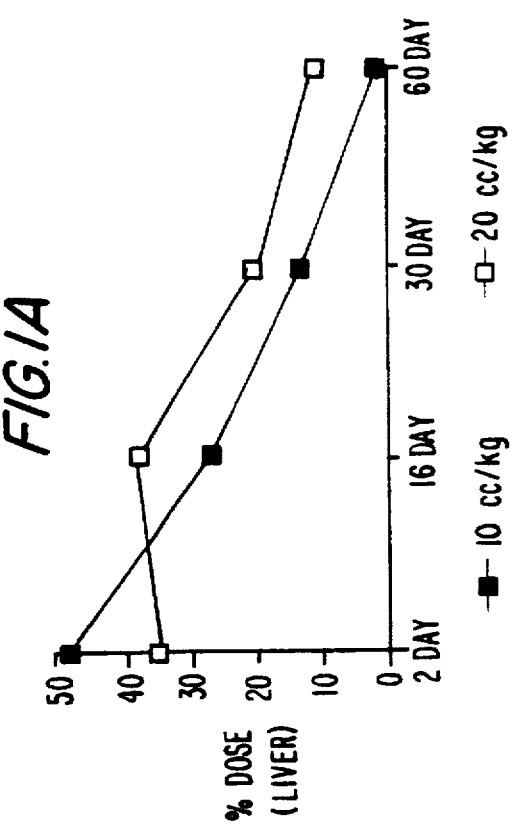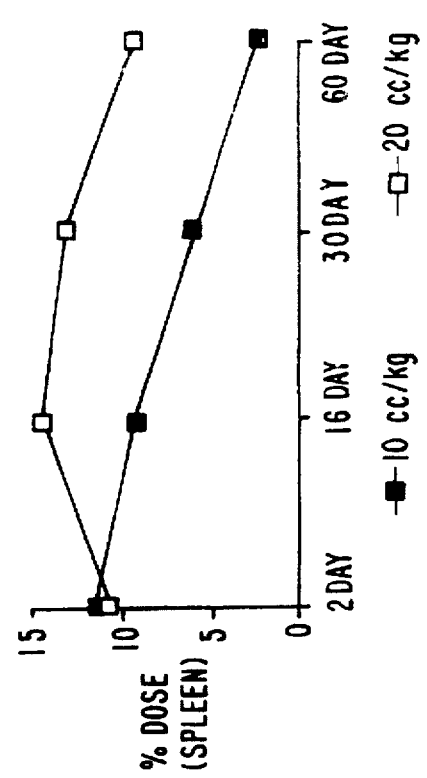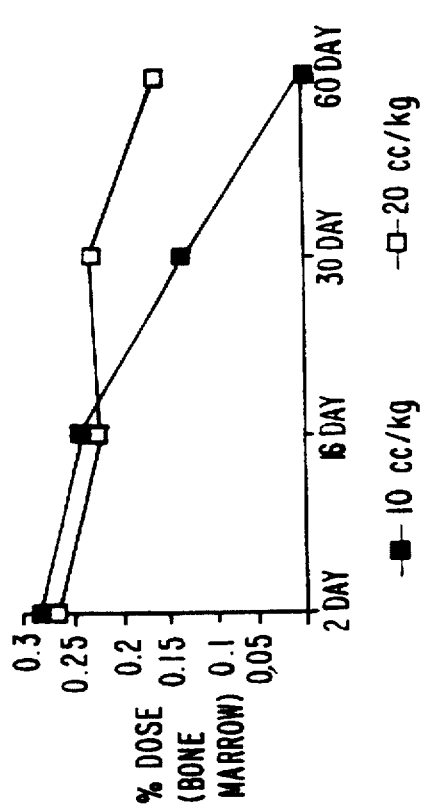

HIGHLY FLUORINATED, CHLORO-SUBSTITUTED ORGANIC COMPOUND-CONTAINING EMULSIONS AND METHODS OF MAKING AND USING THEM

This application is a 371 of PCT/US92/10736, filed Dec. 11, 1992, which is a continuation-in-part of U.S. application Ser. No. 07/806,692, filed Dec. 12, 1991, now U.S. Pat. No. 5,403,575.

TECHNICAL FIELD OF INVENTION

This invention relates to compositions comprising highly fluorinated, chloro-substituted, non-cyclic organic compounds having 7 to 9 carbon atoms and to processes of making and using them. More particularly, this invention relates to emulsions comprising those highly fluorinated, chloro-substituted organic compounds. This invention also relates to emulsions comprising non-cyclic perfluorochloroethers having 7 to 10 carbon atoms, preferably 7 to 9 carbon atoms. These novel emulsions have various medical and oxygen transport applications. They are especially useful medically as contrast media for various biological imaging modalities, such as nuclear magnetic resonance, $^{19}$F-magnetic resonance imaging, ultrasound, x-ray, computed tomography and position emission tomography, as oxygen transport agents or "artificial bloods," in the treatment of heart attack, stroke, and other vascular obstructions, as adjuvants to coronary angioplasty and in cancer radiation treatment and chemotherapy.

BACKGROUND OF THE INVENTION

Highly fluorinated organic compounds, and particularly perfluorocarbon compounds, are well known to be both stable and chemically inert. During the past 20 years much attention has focused on the use of such compounds in biological systems because they are capable of dissolving and transporting large amounts of oxygen. These properties make them potentially useful as contrast media, oxygen transport agents or "artificial bloods", in the treatment of heart attack, stroke, and other vascular obstructions, as adjuvants to coronary angioplasty, and in cancer radiation treatment and chemotherapy.

Among the highly fluorinated organic compounds that are said to be useful in such applications are perfluorocarbon compounds, e.g., perfluorodecalin, perfluoroindane, perfluorotrimethyl bicyclo [3.3.1] nonane, perfluoromethyl adamantane, perfluorodimethyl adamantane, and perfluoro-2,2,4,4-tetramethylpentane; 9–12C perfluoro amines, e.g., perfluorotripropyl amine, perfluorotributyl amine, perfluoro-1-azatricyclic amines; bromofluorocarbon compounds, e.g., perfluorooctyl bromide and perfluorooctyl dibromide; F-4-methyl octahydroquinolidizine and perfluoro ethers, including chlorinated polyfluorocyclic ethers. Such compounds are described, for example, in U.S. Pat. Nos. 3,962,439, 3,493,581, 4,110,474, 4,186,253, 4,187, 252, 4,252,827, 4,423,077, 4,443,480, 4,534,978, 4,686,024, 4,865,836, 4,866,096 and 4,868,318, European patent applications 80716 and 158,996, British patent specification 1,549,038 and German Offen. 2,650,586.

For intravenous use, highly fluorinated organic compounds must be dispersed as emulsions. See, 35 e.g., L. C. Clark, Jr. et al., "Emulsions Of Perfluorinated Solvents For Intravascular Gas Transport," *Fed. Proc.*, 34(6), pp. 1468–77 (1975); K. Yokoyama et al., "A Perfluorochemical Emulsion As An Oxygen Carrier," *Artif. Organs (Cleve)*, 8(1), pp. 34–40 (1984); and U.S. Pat. Nos. 4,110,474 and 4,187,252. Neat, highly fluorinated organic compounds are immiscible in blood.

Such emulsions must not only contain a high enough concentration of the highly fluorinated organic compound to be effective in the desired level of oxygen transport, they must also by capable of sterilization, preferably by heat, have long term stability in the fluid or non-frozen state, persist for sufficiently long times in the blood stream to deliver useful quantities of oxygen and yet be eliminated rapidly enough from the body to avoid toxicity and retention in body parts and organs.

SUMMARY OF THE INVENTION

This invention relates to novel compositions comprising highly fluorinated, chloro-substituted, non-cyclic organic compounds having 7 to 9 carbon atoms and to processes of making and using them. More particularly, this invention relates to novel highly fluorinated, chloro-substituted organic compound-containing emulsions.

The emulsions of this invention are useful in various oxygen transport applications. They are particularly useful in medical applications, e.g., as contrast media for various biological imaging modalities, including nuclear magnetic resonance, ultrasound, $^{19}$F-magnetic resonance imaging, x-ray, computed tomography, and position emission tomography, as oxygen transport agents or "artificial bloods", in the treatment of heart attack, stroke, and other vascular obstructions, as adjuvants to coronary angioplasty a cancer radiation and chemotherapy.

BRIEF DESCRIPTION OF THE DRAWINGS

FIG. 1 depicts the percent dose of PFBCBE remaining in tissue at 2, 16, 30 and 60 days post-infusion.

DETAILED DESCRIPTION OF THE INVENTION

In order that the invention herein described may be more fully understood, the following detailed description is set forth.

The present invention relates to various highly fluorinated, chloro-substituted organic compounds ("chlorofluorochemicals"). These compounds, particularly, emulsions containing them, are useful in various medical and oxygen transport applications. The highly fluorinated, chloro-substituted, organic compounds of this invention contain 7 to 9 carbon atoms, are non-cyclic, and include, for example, highly fluorinated chlorochemicals, particularly, chloroperfluorochemicals, including perfluorochloroethers, and highly fluorinated bromochlorochemicals, particularly, bromochloroperfluorochemicals. We prefer perfluorochlorochemicals.

The compounds of this invention typically, contain one to three chloro or bromo substituents in total, at least one being chloro. Preferably, only chloro substituents are present. More preferably, the compounds of this invention have two chloro substituents.

Although the chloro and bromo substituents can in principle be located on any carbon in the compound, we prefer that when there is more than one such substituent, that they be on different carbons (i.e., not geminal). In the most preferred chlorofluorochemical of this invention—1,8 perfluorodichlorooctane—the chloro substituents are located at opposite ends of the carbon chain. One route of synthesis of this compound is described in A. Y. Zapevalov et al., "Synthesis And Reactions Of Oxygen-Containing Organofluorine Compounds VI. Polyfluorinated Ketones With A Trifluoromethyl Group", *Journal of Organic Chemistry of the USSR*, 14, pp. 239–242 (July 1978).

This invention also contemplates N-, O-, and S-containing highly fluorinated, chloro-substituted, non-cyclic organic-compounds having 7 to 9 carbon atoms. For example, tertiary amines, ethers or sulfones may be employed. It should be understood that any of the highly fluorinated, chloro-substituted organic compounds of this invention may be mixed together or with other well known highly fluorinated organic compounds and used in the emulsions of this invention.

The highly fluorinated, chloro-substituted organic compounds of this invention are non-cyclic, straight or branched chain compounds having 7 to 9 carbon atoms, preferably saturated aliphatic compounds. Compounds having 8 carbon atoms are preferred. Dichloro-substituted organic compounds having 8 carbon atoms, e.g., perfluorodichlorooctane and perfluoro-bis-chlorobutyl ether, are more preferred. The most preferred compound in accordance with this invention is 1,8-perfluorodichlorooctane ("PFDCO").

In addition, this invention also contemplates perfluorochloroethers having 7 to 10 carbons, and more preferably perfluorochloroethers having 7 to 9 carbon atoms. The perfluorochloroethers contemplated within the scope of this invention include: $[Cl-(CF_2)_4-O-]_2CF_2$, $[Cl-(CF_2)_3-O-]_2CFCF_3$, $[Cl-C_2F_4-O-C_2F_4-O-]_2CF_2$, $C_4F_9-O-)_2CFCF_2-Cl$, $C_5F_{11}-O-CF(CF_2-Cl)_2$, $[(Cl-CF_2)_2CF-O-]_2CF_2$, $C_4F_9-O-C(CF_2-Cl)_3$, $Cl-CF_2C(CF_3)_2CF_2-O-(CF_2)_4-Cl$, $Cl-C_2F_4-O-CF(CF_3)CF(CF_3)-O-C_2F_4-Cl$, $C_8F_{17}-O-CF_2-Cl$, $C_5F_{11}-O-(CF_2)_5-Cl$, $CF_3-O-(CF_2)_8-Cl$, $Cl-C_2F_4-O-(CF_2)_4-O-C_2F_4-Cl$, $Cl-(CF_2CF_2-O-)_3C_2F_4-Cl$, $(CF_3)_3C-O-(CF_2)_5-Cl$, $C_4F_9-O-CF_2CF(CF_2-Cl)-O-CF_3$, $C_4F_9-O-C_2F_4-O-C_2F_4-Cl$, $C_6F_{13}-O-C_2F_4-O-C_2F_4-Cl$, and perfluoro-bis-chlorobutyl ether. We prefer $C_4F_9-O-C_2F_4-O-C_2F_4-Cl$, $C_6F_{13}-O-C_2F_4-O-C_2F_4-Cl$ and perfluoro-bis-chlorobutyl ether, most preferably perfluoro-bis-chlorobutylether.

Several methods exist for fluorination of chloroether or fluorochloroether precursors to produce the perfluorochloroethers that are useful in this invention. Such precursors, e.g., bis-chlorobutylether, butoxyethoxyethylchloride and hexyloxyethoxyethylchloride, are commercially available or can be readily synthesized by one of ordinary skill in the art.

We prefer either solid phase or liquid phase direct fluorination as described in U.S. Pat. Nos. 4,755,567, 4,859,747, 5,093,432, and in published PCT application WO 90/06296. The direct fluorination of the chloroether or fluorochloroether precursors can be carried out at moderate or near ambient temperatures, e.g., $-20°$ C. to $+50°$ C., using a stoichiometric excess of fluorine gas. Preferably the fluorine gas is diluted with an inert gas, such as nitrogen, to minimize or avoid the hazards of pure fluorine gas and to control the amount of heat generated upon initial contact of the precursor with fluorine. The fluorination can be carried out in an oxygen- and water-free environment and can be carried out in the presence of a solid particulate scavenger, e.g., sodium fluoride, for the hydrogen fluoride by-product that is generated.

We prefer to use liquid phase direct fluorination in the absence of a hydrogen fluoride scavenger. The fluorochloroether precursor is dispersed in an inert liquid, such as a fluorocarbon or fluorochlorocarbon liquid. The reaction is conducted at a temperature and inert gas flow rate sufficient to volatilize the hydrogen fluoride by-product and enable its removal from the fluorination zone as it is generated. See, e.g., published PCT application WO 90/06296.

For intravenous use, the highly fluorinated, chloro-substituted organic compounds of this invention are dispersed as emulsions. Such emulsions may comprise up to about 60% (by volume) of the chloro-containing compound. Preferably, the emulsions of this invention comprise from about 10% to about 50% (by volume) of the highly fluorinated, chloro-substituted organic compound. Most preferably, emulsions containing about 25% to about 40% (by volume) of a chlorofluorochemical of this invention are used.

The emulsions of this invention are made using conventional means and methods and include components common to the well known emulsions of highly fluorinated organic compounds. Among the surfactants useful in the emulsions of this invention are any of the known anionic, cationic, nonionic and zwitterionic surfactants. Preferred are the nonionic surfactants, such as alkyl or aryl compounds, whose hydrophilic part consists of polyoxyethylene chains, sugar molecules, polyalcohol derivatives or other hydrophilic groups, for example, any of the BASF Wyandotte formulations of polyoxyethylene and polyoxypropylene oxides sold under the tradename "Pluronic", for example, Pluronic F-68 or F-108, or zwitterionic surfactants. Fluorinated surfactants, e.g., ATSURFS® F-31 (ICI, Wilmington, Del.), may also be used in the emulsions of this invention. See, e.g., Riess et al., "Design, Synthesis and Evaluation of Fluorocarbons and Surfactants for In Vivo Applications, New Perfluoroalkylated Polyhydroxylated Surfactants", *Artif. Cells Artif. Organs*, 16, pp. 421–30 (1988). Again, combinations of these surfactants may, of course, be used in the emulsions of this invention. In addition, mixtures of compounds, one or more of which are not surfactants, but which compounds when combined act as surfactants may also be usefully employed as the surfactant component of the emulsions of this invention.

Preferably, the surfactants used in the emulsions of this invention are physiologically acceptable, for example, one or more of the following: egg and soybean phosphatides, lecithin, and alkyl salts of oleic acid, such as sodium oleate. More preferable is lecithin. While the amount of a particular surfactant used in the emulsions of this invention depends on the amounts and properties of the other components of the emulsion, typically we employ between about 0.5 and 10% (by weight of the total emulsion) of surfactant. More preferably, we use about 1 to about 4% (by weight).

The emulsions of this invention may also contain an oil that is not substantially surface active and not significantly water soluble. Such oils are, for example, described in EP 231,091, WO 89/10118 and U.S. Pat. No. 4,866,096. They include liquid fatty oils, hydrocarbons, waxes, such as monoesters of a fatty acid and a monohydroxide alcohol, long chain ethers, diglycerides, triglycerides, silicone oils and nitriles. Among the useful oils in these classes are palmitoyl oleate, octyl nitrile, dodecyl nitrile, soy(bean) oil, safflower oil, mineral oil, hexadecane, and diglycerides and triglycerides having a $C_{12-18}$ carbon chain. Of course, any mixture of triglycerides and or oils that are similar in fatty acid composition to triglycerides may be used. These oils may be used singly or in various combinations in the emulsions and processes of this invention. When our emulsions are to be used medically, the oil or combination of oils must, of course, be physiologically acceptable. In that regard, we prefer physiologically acceptable liquid fatty oils, such as soybean and safflower oils.

The amount of oil, or oils, if present, in the emulsions of this invention may vary over a wide range of concentrations depending on the concentration and properties of the other components of the emulsion, being principally dependent on the characteristics of the highly fluorinated, chloro-substituted organic compound component of the emulsion. The actual oil concentration to produce an acceptable emulsion for any given set of components is easily determined as taught by this invention using the simple techniques of preparing the emulsions at various oil concentrations. Within this teaching, we typically employ between about 0.5 and 20 w/v% of oil or a mixture of oils. Preferably, we employ between about 1 and 5 w/v%.

In addition to the highly fluorinated, chloro-substituted organic compounds, oils, surfactants and water, the emulsions of this invention may also contain other components conventionally used in "artificial bloods" or blood substitutes, oxygen transport agents or contrast media. For example, emulsions according to this invention usually also contain an isotonic agent, typically sugars, such as glucose, mannose and fructose, glycerin, or other polyhydric alcohols to adjust the osmotic pressure of the emulsion to about that of blood. Osmolarity may also be adjusted after sterilization by buffers such as sodium chloride, sodium bicarbonate, magnesium chloride, and the like, to reduce the possibility of red blood cell injury. For example, we typically use between about 1 and 2.5% (by weight of the emulsion) of such agents. However, other amounts and other osmotic pressure controlling agents, e.g., Tyrode solution, could as well be used. In addition, these emulsions may be mixed with 0.9% saline, lactated Ringer's solution, and serum and serum products with no adverse effect on emulsion particle size and stability. The emulsions of this invention may also include other components, such as osmotic agents, e.g., dextran or hydroxyethyl-starch (HES), and antioxidants.

In the most preferred emulsions of this invention, the chlorofluorochemical is PFDCO, the surfactant is egg yolk lecithin, and the oil, if present, is safflower oil. Glycerin is typically added to the emulsion to adjust isbtonicity. In the most preferred emulsions of this invention, the PFDCO is present in about 40% by volume, the lecithin in about 2.0 w/v%, and the safflower oil, if present, in about 2.0 w/v% of the emulsion.

As described above, the highly fluorinated, chloro-substituted organic compound-containing emulsions of this invention are useful as contrast media. Lacking hydrogen, they produce a signal void in the selected body part which can be distinguished from adjacent body parts by various biological imaging modalities, e.g., nuclear magnetic resonance, ultrasound, x-ray, computed tomography and position emission tomography. In addition, the compounds of this invention and their emulsions are useful as contrast agents and for direct imaging in $^{19}$F-MRI.

When used as contrast media, the emulsions of the invention may be administered, for example, by bolus, orally, subcutaneously, intraperitoneally, intrathecally, or other medically approved method of administration, e.g., catheterization, to the degree necessary such that the emulsions are capable of producing clear concise shadows of the desired part or parts of the anatomy.

The emulsions of this invention may also be used as artificial bloods and infused intravenously to animals or humans suffering from blood loss or oxygen depleted blood. Accordingly, the emulsions of this invention may also be used to sustain the oxygen requirements of living organisms or their cellular constituents, e.g., cell lines. Besides the utility of such artificial bloods for animals and humans, these emulsions can be used as a perfusate for the preservation of internal organs, such as with organ transplants, for extended periods outside the body.

Publications demonstrating the usefulness of highly fluorinated organic compound-containing emulsions to preserve organs outside the body of a human or an animal include Kawamura et al., "A New Simple Two layer (Euro-Collins' Solution/Perfluorochemical) Cold Storage Method For Pancreas Preservation", *Transplantation Proc.*, 21, pp. 1376–77 (1989); Segel and Ensunsa, "Albumin Improves Stability And Longevity Of Perfluorochemical-Perfused Hearts", *Am. J. Physiol.*, 254, pp. H1105–12 (1988); Segel et al., "Prolonged Support of Working Rabbit Hearts Using Flusol-43 Or Erythrocyte Media", *Am. J. Physiol.*, 252, pp. H349–59 (1987); Segel and Rendig, "Isolated Working Rat Heart Perfusion With Perfluorochemical Emulsion Fluosol-43", *Am. J. Physiol.*, 242, pp. H485–89 (1982). The chlorofluorochemicals and emulsions of this invention are similarly useful.

The ability of highly fluorinated organic compounds to carry oxygen make them useful when dispersed as emulsions to enhance cancer radiation treatment and chemotherapy, in coronary balloon angioplasty, and in the treatment of heart attack, stroke and other vascular obstructions. Publications demonstrating the usefulness of such emulsions to enhance cancer radiation treatment and chemotherapy include Teicher and Rose, "Oxygen-Carrying Perfluorochemical Emulsion As An Adjuvant To Radiation Therapy In Mice", *Cancer Res.*, 44, pp. 4285–88 (1984); Teicher and Rose, "Effects Of Dose And Scheduling On Growth Delay Of The Lewis Lung Carcinoma Produced By The Perfluorochemical Emulsion, Fluosol-DA", *Int. J. Radiation Oncology Biol. Phys.*, 12, pp. 1311–13 (1986); Rockwell et al., "Reactions of Tumors And Normal Tissues In Mice To Irradiation In The Presence And Absence Of A Perfluorochemical Emulsion", *Int. J. Radiation Oncolovy Biol. Phys.*, 12, pp. 1315–18 (1986); Teicher and Rose, "Perfluorochemical Emulsions Can Increase Tumor Radiosensitivity", *Science*, 223, pp. 934–36 (1984); Teicher et al., "Effect Of Various Oxygenation Conditions And Fluosol-DA On Cytotoxicity And Antitumor Activity Of Bleomycin In Mice", *J. Natl. Cancer Inst.*, 80, pp. 599–603 (1988). The chlorofluorochemicals and emulsions of this invention are similarly useful.

Publications demonstrating the usefulness of highly fluorinated organic compound-containing emulsions to minimize the adverse effects of coronary balloon angioplasty include Virmani et al., "Myocardial Protection By Perfluorochemical Infusion During Transient Ischemia Produced By Balloon Coronary Occlusion", *Am. Heart J.*, 116, pp. 421–31 (1988); Jaffe et al., "Preservation Of Left Ventricular Ejection Fraction During Percutaneous Transluminal Coronary Angioplasty By Distal Transcatheter Coronary Perfusion of Oxygenated Fluosol DA 20%", *Am. Heart J.*, 115, pp. 1156–64 (1988); Cleman et al., "Prevention of Ischemia During Percutaneous Transluminal Coronary Angioplasty By Transcatheter Infusion Of Oxygenated Fluosol DA 20%", *Circulation*, 74, pp. 555–62 (1986); Anderson et al., "Distal Coronary Artery Perfusion During Percutaneous Transluminal Coronary Angioplasty", *Am. Heart J.*, 110, pp. 720–26 (1984). The chlorofluorochemicals and emulsions of this invention are similarly useful.

Publications demonstrating the usefulness of highly fluorinated organic compound-containing emulsions for treating heart attack, stroke and vascular occlusions include Peerless et al., "Modification of Cerebral Ischemia With Fluosol", *Stroke*, 16, pp. 38–43 (1985); Osterholm et al., "Severe Cerebral Ischemia Treatment By Ventriculosubarachnoid Perfusion With An Oxygenated Fluorocarbon Emulsion", *Neurosurg.*, 13, pp. 381–87 (1983); Peerless et al., "Protective Effect of Fluosol-DA In Acute Cerebral Ischemia", *Stroke*, 12, pp. 558–63 (1981); Forman et al., "Reduction Of Infarct Size With Intracoronary Perfluorochemical In A Canine Preparation of Reperfusion", *Circulation*, 71, pp. 1060–68 (1985). The chlorofluorochemicals and emulsions of this invention are similarly useful.

The emulsions of this invention may be prepared by conventional mixing of the highly fluorinated components (discontinuous phase) with an aqueous (continuous) phase and a surfactant. Alternatively, the emulsions of this invention may be prepared by mixing an aqueous phase with any suitable surfactant, and optionally, osmotic agents, buffering agents, electrolytes if desired, other emulsifying agents, additional anti-oxidants, and the like into an aqueous dispersion. The highly fluorinated components may then be mixed into the aqueous dispersion so as to provide an emulsion of this invention.

The emulsions of this invention may also be prepared by pre-mixing an aqueous dispersion with any suitable surfactant(s) and, optionally, other conventional components of artificial bloods, e.g., osmotic agents and the like. The oil, if present, may then be mixed into the above-described aqueous dispersion at a predetermined rate. The highly fluorinated components may then be mixed in at a predetermined rate so as to provide an emulsion of this invention.

The resulting emulsion is sterilized, preferably at temperatures in excess of 115° C., more preferably at about 121° C., packaged and otherwise processed for storage and use.

The mixing, pre-mixing if desirable, and emulsification of the components may be done using any of the conventional mixers, homogenizers, and emulsifiers. For example, one may employ Fisher brand touch mixers and microfluidizers or Gaulin homogenizers. In preparing the emulsions of this invention, we prefer to use an inert atmosphere (e.g., $N_2$) to prevent degradation of the surfactant and fatty oils, if present, and to use temperatures between about 45° C. and 55° C.

In order that this invention be more fully understood, preferred emulsions prepared and used in accordance with the description of this invention are provided below by way of example.

EXAMPLES

Preparation Of Emulsion (Method A)

Powdered, refined, egg yolk lecithin was obtained from Kabi Vitrum and dispersed in sterile $H_2O$ (Millipore®) under an inert atmosphere ($N_2$) using a Waring™ Blender at high speed for 2–3 minutes. The lecithin so dispersed was collected under an inert atmosphere and stored at 4° C. All lecithin dispersions so prepared were used within one week of their preparation.

The lecithin dispersion (18.00% by weight) was suspended by vigorous handshaking and then a 17.01 g portion was transferred to a 250 ml inlet reservoir, again under an inert atmosphere, which fed a Microfluidizer™ homogenizer. The lecithin dispersion was then further diluted with 81.85 g of water and 2.94 g of glycerin prior to starting the homogenizer. The homogenizer was then started and the pressure was maintained at about 8000 psi at a flow rate of about 350 ml/min. for about 2 minutes. Oil (3.50%) was slowly introduced (1–2 minutes) in an adjacent port, below the level of the inlet reservoir, as close to the homogenizer inlet as possible. The chlorofluorochemical (117.6 g, 70.0 ml) was slowly added (6–10 minutes) through the same adjacent port. The homogenate was cycled through the valves of homogenizer for about an additional 15 minutes. The pH was maintained at about 8.5 or higher by the controlled addition of 0.47 M $Na_2CO_3$ or other base. The resulting emulsion, comprising 1.75 w/v% lecithin, 2.0 v/v% oil, and 40.0 v/v% chlorofluorochemical, was then sterilized in a rotating steam autoclave at about 121° C. for about 15 minutes.

Preparation of Emulsion (Method B)

A one quart Waring™ blender was first loaded with the appropriate charge of sterile water (137.0 g), glycerin (4.09 g), lecithin (5.07 g), surfactant (5.02 g), and chlorofluorochemical (177.05 g, 98.91 ml) and mixed at high speed for 2–3 minutes. The entire contents were then added to a 250 ml inlet reservoir in a Microfluidizer™ homogenizer. The homogenizer was started and the pressure was maintained at about 8000 psi at a flow rate of about 350 ml/min. The pH was maintained at about 8.00 or higher by controlled addition of 0.47 M $Na_2CO_3$ or other base. The material was cycled through the homogenizer for about 15 minutes. In the case of larger batches (>500 ml), the emulsion was alternately cycled between two different vessels for a total of six passes. The resulting emulsion, comprising 1.24 w/v% glycerin, 2.01 w/v% lecithin, 1.99 w/v% surfactant and 38.23 v/v% chlorofluorochemical, was then sterilized in a rotating steam autoclave at about 121° C. for about 15 minutes.

Preparation of Emulsion (Method C)

Water (about 3000.0 g) was placed in a 5 liter vessel equipped with a high speed stirrer, nitrogen inlet, and solids addition inlet. The stirrer was started and about 270.70 g of lecithin and about 257.7 g of oil were added to the vessel and maintained under Nitrogen atmosphere. Blending continued at about 1800 rpm for about 15 minutes. During this time, the ingredients formed a coarse emulsion. This coarse emulsion was transferred to a 14 Liter vessel equipped with a low speed stirrer, nitrogen inlet, water cooling jacket and feed line. With mild agitation, about 4139.80 g of water was added, followed by a 5% solution of aqueous sodium carbonate (about 56.6 g). A Gaulin M15R homogenizer valve was set to an operational pressure of about 7500–9000 psi and the coarse emulsion was recirculated through this valve while about 9104.90 g of chlorofluorochemical was added to the mixture, prior to the homogenizer valve, at a rate of about 15 g/min. After addition of the chlorofluorochemical was complete, the entire emulsion was cycled into an alternate 14 Liter vessel (equipped identically to the first) with homogenization continuing at the aforementioned valve pressure of about 7500–9000 psi. The homogenate was passed through the homogenizing valve for about ten cycles, each cycle being passed into an alternate vessel. During this time, the temperature of the homogenate was maintained between about 30° C. (at the inlet side of the valve) and 53° C. (at the outlet side of the valve) by the application of cooling water to the vessel jackets. The emulsion was collected, bottled into 350 mL containers, and sterilized for 15 minutes at 121° C. in an autoclave equipped with a rotating basket.

Of the methods described above, the particular method employed in the preparation of the following illustrative emulsions is indicated in brackets. In Examples 1–9 and 11, the chlorofluorochemical emulsions were prepared on a small scale in microfluidizers at a pressure of between about 7,000 and 9,000 psig for 10 to 15 minutes. Example 10 was prepared on a large scale in a Gaulin homogenizer. The components of the aqueous phase which typically comprise about 60% by volume of these emulsions are not shown.

Emulsion DBF02-76 (PFCN)* [A]

Post Sterilization

| Ingredient | w/w % | w/v % | v/v % |
|---|---|---|---|
| lecithin | 1.35 | 1.77 | 1.77 |
| safflower oil | 1.51 | 1.99 | 2.16 |
| glycerin | 1.23 | 1.61 | 1.28 |
| PFCN | 53.73 | 70.54 | 39.41 |

| | pH | Osm[b] | Visc[c] | PSD[d] |
|---|---|---|---|---|
| pre-sterilization | 9.02 | 308 | 5.66 | 260 |
| post-sterilization | 8.24 | 311 | 7.41 | 267 |

*Perfluorochlorononane.
[b]Osmolarity (milliosmols)
[c]Viscosity at 37° C. (centistokes)
[d]Particle Size Distribution mean by laser light scatterer (nanometers)

Emulsion DBF2-78 (PFCO)* [A]

Post Sterilization

| Ingredient | w/w % | w/v % | v/v % |
|---|---|---|---|
| lecithin | 1.36 | 1.79 | 1.79 |
| safflower oil | 1.54 | 2.02 | 2.20 |
| glycerin | 1.23 | 1.62 | 1.28 |
| PFCO | 53.87 | 70.79 | 39.55 |

| | pH | Osm | Visc | PSD |
|---|---|---|---|---|
| pre-sterilization | 8.86 | 308 | 7.78 | 251 |
| post-sterilization | 8.25 | 314 | 6.85 | 309 |

*Perfluorochlorononane.

Emulsion RAS6-54 (PFDCO)* [B]

Post Sterilization

| Ingredient | w/w % | w/v % | v/v % |
|---|---|---|---|
| lecithin | 1.53 | 2.02 | 2.02 |
| safflower oil | 1.51 | 1.99 | 2.16 |
| glycerin | 1.30 | 1.71 | 1.35 |
| PFDCO | 53.82 | 70.72 | 39.51 |

| | pH | Osm | Visc | PSD |
|---|---|---|---|---|
| pre-sterilization | 8.85 | 3.34 | 9.22 | 187 |
| post-sterilization | 8.58 | 3.27 | 7.98 | 199 |

*Perfluorodichlorooctane(1,8-perfluorodichlorooctane)

Emulsion RAS6-56 (PFDCO) [B]

Post Sterilization

| Ingredient | w/w % | w/v % | v/v % |
|---|---|---|---|
| lecithin | 1.53 | 2.01 | 2.01 |
| safflower oil | 1.47 | 1.93 | 2.10 |
| glycerin | 1.23 | 1.62 | 1.28 |
| PFDCO* | 53.98 | 70.97 | 39.65 |

| | pH | Osm | Visc | PSD |
|---|---|---|---|---|
| pre-sterilization | 8.80 | 2.83 | 6.05 | 184 |
| post-sterilization | 8.35 | 2.78 | 5.93 | 196 |

*included isomers

Emulsion RAS9-12 (PFDCO) [B]

Post Sterilization

| Ingredient | w/w % | w/v % | v/v % |
|---|---|---|---|
| lecithin | 3.04 | 3.98 | 4.33 |
| safflower oil | 0.00 | 0.00 | 0.00 |
| glycerin | 1.23 | 1.61 | 1.28 |
| PFDCO | 53.64 | 70.26 | 39.25 |

| | pH | Osm | Visc | PSD |
|---|---|---|---|---|
| pre-sterilization | 8.69 | 330 | 7.33 | 174 |
| post-sterilization | 8.20 | 336 | 7.46 | 213 |

Emulsion RAS9-14 (PFDCO) [B]

Post Sterilization

| Ingredient | w/w % | w/v % | v/v % |
|---|---|---|---|
| lecithin | 0.38 | .50 | .55 |
| safflower oil | 0.00 | 0.00 | 0.00 |
| glycerin | 1.25 | 1.65 | 1.31 |
| PLURONIC | 2.67 | 3.51 | 3.51 |
| PFDCO | 53.86 | 70.87 | 39.59 |

| | pH | Osm | Visc | PSD |
|---|---|---|---|---|
| pre-sterilization | 8.30 | 307 | 21.70 | 187 |
| post-sterilization | 7.76 | 325 | 8.95 | 311 |

Emulsion RAS9-18 (1,2 PFDCO) [B]

Post Sterilization

| Ingredient | w/w % | w/v % | v/v % |
|---|---|---|---|
| lecithin | 1.51 | 1.97 | 1.97 |
| safflower oil | 1.50 | 1.97 | 2.14 |
| glycerin | 1.26 | 1.65 | 1.31 |
| 1,2 PFDCO* | 53.36 | 69.91 | 39.06 |

| | pH | Osm | Visc | PSD |
|---|---|---|---|---|
| pre-sterilization | 7.96 | 336 | 6.96 | 172 |
| post-sterilization | 6.99 | 337 | 5.63 | 192 |

*1,2 Perfluorodichlorooctane, included isomers

Emulsion RAS10-28 (PFDCO) [B]

Post Sterilization

| Ingredient | w/w % | w/v % | v/v % |
|---|---|---|---|
| lecithin | 0.38 | 0.50 | 0.50 |
| Pluronic F-68 | 2.67 | 3.50 | 3.50 |
| safflower oil | 0.00 | 0.00 | 0.00 |

Emulsion RAS10-28 (PFDCO) [B]

| | | | |
|---|---|---|---|
| glycerin | 1.24 | 1.64 | 1.30 |
| PFDCO | 54.19 | 71.32 | 39.84 |

| | pH | Osm | Visc | PSD |
|---|---|---|---|---|
| pre-sterilization | 8.59 | 314 | 17.70 | 201 |
| post-sterilization | 8.23 | 322 | 9.35 | 345 |

Emulsion RAS10-30 (PFDCO) [B]

Post Sterilization

| Ingredient | w/w % | w/v % | v/v % |
|---|---|---|---|
| lecithin | 2.56 | 3.50 | 3.50 |
| safflower oil | 0.00 | 0.00 | 0.00 |
| glycerin | 1.29 | 1.69 | 1.34 |
| PFDCO | 53.59 | 70.36 | 39.31 |

| | pH | Osm | Visc | PSD |
|---|---|---|---|---|
| pre-sterilization | 8.95 | 327 | 6.81 | 202 |
| post-sterilization | 8.42 | 333 | 8.45 | 227 |

Emulsion RAS10-18 (PFDCO) [C]

Post Sterilization

| Ingredient | w/w % | w/v % | v/v % |
|---|---|---|---|
| lecithin | 1.61 | 2.09 | 2.09 |
| safflower oil | 1.53 | 1.99 | 2.16 |
| PFDCO | 54.10 | 70.31 | 40.18 |

| | pH | Osm | Visc | PSD |
|---|---|---|---|---|
| pre-sterilization | 8.65 | * | * | 260 |
| post-sterilization | 7.86 | * | * | 257 |

*not calculated in a non-glycerin-containing emulsion

EXAMPLE 11

Perfluorochloroethers

The quantity of lecithin, safflower oil and perfluorochloroether (PFCE) in each emulsion (A-G) is equivalent to 2.00±0.05 w/v% lecithin, 2.00±0.05 w/v% safflower oil, and 40±2 v/v% PFCE. The perfluorochloroethers in emulsions A-G were synthesized from fluorochlorether precursors using liquid phase direct fluorination. The pH of the composition was adjusted to 7.5 to 9.0 with 5% aqueous sodium carbonate monohydrate prior to sterilization at 121° C. for 15 minutes. The emulsions are both reproducible and stable to heat sterilization.

Perfluorochloroether Emulsions [B]

| Emulsion | Lecithin (g) | Oil (g) | Glycerin (g) | $Na_2CO_3.H_2O$ (g) | $H_2O$ (g) | PFCE (g) |
|---|---|---|---|---|---|---|
| A (RAS7-62)[a] | 5.02 | 4.94 | 4.08 | 0.048 | 137.1 | 172.64 |
| B (RAS9-4)[a] | 22.00 | 21.7 | 18.07 | 0.20 | 601.9 | 776.80 |
| C (RAS9-6)[a] | 7.01 | 6.97 | 5.85 | 0.097 | 191.1 | 242.55 |
| D (RAS9-30)[a] | 7.00 | 6.94 | 5.83 | 0.074 | 192.0 | 242.07 |
| E (RAS9-44)[a] | 16.98 | 16.81 | 14.26 | 0.19 | 463.4 | 589.94 |
| F (RWF12-96)[b] | 5.05 | 4.95 | 4.22 | 0.028 | 136.6 | 166.17 |
| G (RWF12-98)[c] | 5.46 | 5.36 | 4.47 | 0.033 | 147.80 | 186.03 |

| | pH | Osm | Visc | PSD |
|---|---|---|---|---|
| Emulsion A | | | | |
| pre-sterilization | 8.69 | 313 | 8.65 | 220 |
| post-sterilization | 8.09 | 316 | 7.98 | 236 |
| Emulsion B | | | | |
| pre-sterilization | 8.45 | 348 | 10.6 | 213 |
| post-sterilization | 7.65 | 346 | 9.87 | 215 |
| Emulsion C | | | | |
| pre-sterilization | 8.85 | 339 | 9.02 | 201 |
| post-sterilization | 8.33 | 334 | 8.13 | 216 |
| Emulsion D | | | | |
| pre-sterilization | 8.82 | 329 | 8.90 | 216 |
| post-sterilization | 8.36 | 330 | 8.45 | 232 |
| Emulsion E | | | | |
| pre-sterilization | 8.71 | 342 | 11.3 | 245 |
| post-sterilization | 8.03 | 343 | 10.9 | 266 |
| Emulsion F | | | | |
| pre-sterilization | 8.10 | 324 | 5.81 | 264 |
| post-sterilization | 7.59 | 319 | 5.90 | 264 |

| Emulsion G | | | | |
|---|---|---|---|---|
| pre-sterilization | 8.28 | 327 | 7.50 | 266 |
| post-sterilization | 7.77 | 320 | 7.31 | 273 |

$^a$perfluoro-bis-chlorobutyl ether (PFBCBE) Cl—C$_4$F$_8$—O—C$_4$F$_8$—Cl.
$^b$C$_4$F$_9$—O—C$_2$F$_4$—O—C$_2$F$_4$—Cl.
$^c$C$_6$F$_{13}$—O—C$_2$F$_4$—O—C$_2$F$_4$—Cl.

To model stability in the human circulation, emulsions A, B and E were admixed 1:1 with a 5% solution of human serum albumin in lactated Ringer's solution. After incubation in this medium for 4 days at 37° C., the mean particle size distribution was 289 nanometers for example A, 265 nanometers for example B and 263 nanometers for example E. The emulsions are clearly stable under these conditions as well.

EXAMPLE 12

Emulsion C (Example 11) was infused intravenously into two groups of 200–250 g albino Sprague Dawley male rats at a rate of 1 cc/min to a total dose of 10 cc/kg (40 animals) or 20 cc/kg (20 animals). One quarter of each group was sacrificed at 2, 16, 30, and 60 days post-infusion. The clearance of perfluoro-bis-chlorobutyl ether (PFBCBE) was measured by analyzing the liver, lung, spleen, and bone marrow from each animal. The tissue was ground in a Tissuemizer, extracted with an organic solvent, e.g., chloroform, carbontetrachloride or trifluoro-trichloro ethane, and analyzed by gas chromatography.

FIG. 1 depicts the average percent dose of PFBCBE remaining in each of the four organs at each timepoint post-infusion. Nearly all of the perfluorocarbon cleared the major tissues by 60 days in rats receiving a total of 10 cc/kg PFBCBE, and is obviously in the process of elimination in rats receiving a dose of 20 cc/kg PFBCBE. Thus, PFBCBE emulsions clear the body at an acceptable rate.

While we have hereinbefore described various embodiments of our invention, it should be apparent that other embodiments also exist within the scope of the invention. Therefore, it should be understood that the scope of this invention is to be defined by the claims rather than the specific embodiments which have been presented hereinbefore by way of example.

We claim:

1. An emulsion comprising perfluoro-bis-chlorobutylether.

2. The emulsion according to claim 1 wherein the perfluoro-bis-chlorobutylether is present in an amount up to about 60% by volume.

3. The emulsion according to claim 1 wherein the perfluoro-bis-chlorobutylether is present in an amount from about 10% to about 50% by volume.

4. The emulsion according to claim 3 wherein the perfluoro-bis-chlorobutylether is present in an amount from about 25% to about 40% by volume.

5. The emulsion according to claim 1 further comprising a surfactant.

6. The emulsion according to claim 5 wherein the surfactant is a physiologically acceptable surfactant.

7. The emulsion according to claim 6 wherein the surfactant is lecithin.

8. The emulsion according to claim 7 further comprising an oil that is not substantially surface active and not significantly water soluble.

9. The emulsion according to claim 8 wherein the oil is a physiologically acceptable oil.

10. The emulsion according to claim 9 wherein the oil is selected from the group consisting of safflower oil and soybean oil.

11. The emulsion according to claim 1 further comprising at least one compound selected from the group consisting of isotonic agents, osmotic pressure controlling agents, serum extending agents and antioxidants.

12. An artificial blood comprising an amount of an emulsion according to any one of claims 1 to 4, or 5 to 11, said amount being therapeutically effective for oxygen transport and delivery in humans.

13. A composition for minimizing the adverse effects of coronary angioplasty comprising a therapeutically effective amount of an emulsion according to any one of claims 1 to 4 or 5 to 11.

14. A contrast agent for biological imaging comprising an amount of an emulsion according to any one of claims 1 to 4 or 5 to 11, said amount being clinically effective for imaging by x-ray, ultrasound, computed tomography, nuclear magnetic resonance, $^{19}$F-magnetic resonance imaging or positron emission tomography.

15. A composition for enhancing cancer radiation treatment and chemotherapy comprising a therapeutically effective amount of an emulsion of any one of claims 1 to 4 or 5 to 11.

16. A composition for preserving organs comprising a preserving effective amount of an emulsion according to any one of claims 1 to 4 or 5 to 11.

17. A composition for treating heart attack, stroke and vascular occlusions comprising a therapeutically effective amount of an emulsion according to any one of claims 1 to 4 or 5 to 11.

18. A method for sustaining the oxygen requirements of living organisms or their cellular constituents comprising the step of administering to a patient in a therapeutically acceptable manner an emulsion according to claim 12.

19. A method for minimizing the adverse effects of coronary balloon angioplasty by perfusion of an emulsion according to claim 13 through the central lumen of the catheter.

20. A method for biological imaging of internal organs and bloodflow using the contrast agent of claim 14 in conjunction with x-ray, computed tomography, ultrasound, magnetic resonance imaging, $^{19}$F-magnetic resonance imaging, or positron emission tomography.

21. A method for enhancing cancer radiation and chemotherapy comprising the step of administering to a patient in a therapeutically acceptable manner an emulsion according to claim 15.

22. A method for preserving organs by perfusion of an emulsion according to claim 16.

23. A method for treating heart attack, stroke and vascular occlusions comprising the step of administering to a patient in a therapeutically acceptable manner an emulsion according to claim 17.

\* \* \* \* \*

UNITED STATES PATENT AND TRADEMARK OFFICE
CERTIFICATE OF CORRECTION

PATENT NO. : 5,785,950
DATED : July 28, 1998
INVENTOR(S) : Kaufman et al.

It is certified that error appears in the above-identified patent and that said Letters Patent is hereby corrected as shown below:

```
Col.  9, line  1, insert --EXAMPLE 1--.
Col.  9, line 24, insert --EXAMPLE 2--.
Col.  9, line 36, change "308' to --314--.
Col.  9, line 40, insert --EXAMPLE 3--.
Col.  9, line 56, insert --EXAMPLE 4--.
Col. 10, line 10, insert --EXAMPLE 5--.
Col. 10, line 25, insert --EXAMPLE 6--.
Col. 10, lile 41, insert --EXAMPLE 7--.
Col. 10, line 58, insert --EXAMPLE 8--.
Col. 11, line 15, insert --EXAMPLE 9--.
Col. 12, line  1, insert --EXAMPLE 10--.
```

Signed and Sealed this

Eighth Day of December, 1998

Attest:

BRUCE LEHMAN

*Attesting Officer*    *Commissioner of Patents and Trademarks*